United States Patent

Graham et al.

(10) Patent No.: US 6,340,981 B1
(45) Date of Patent: *Jan. 22, 2002

(54) METHOD AND APPARATUS FOR STROKE SUBSTITUTION

(75) Inventors: James Graham, Sunnyvale; Jerald Evans, Mountain View, both of CA (US)

(73) Assignee: Sun Microsystems, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/885,617

(22) Filed: Jun. 30, 1997

(51) Int. Cl.[7] ................................................. G09G 5/00
(52) U.S. Cl. ........................ 345/863; 345/764; 345/765; 345/179; 382/303
(58) Field of Search ................................. 345/179, 442, 345/358, 443, 339, 863, 156, 764, 765, 797; 707/541; 382/303

(56) References Cited

U.S. PATENT DOCUMENTS

| 5,202,960 | A | * | 4/1993 | Seiler | 345/443 |
| 5,611,031 | A | * | 3/1997 | Hayashi et al. | 345/442 |
| 5,694,536 | A | * | 12/1997 | Gangnet | 345/442 |
| 5,710,896 | A | * | 1/1998 | Seidl | 345/333 |
| 5,768,607 | A | * | 6/1998 | Drews et al. | 707/512 |
| 5,786,814 | A | * | 7/1998 | Moran et al. | 345/328 |
| 5,845,299 | A | * | 12/1998 | Arora | 345/339 |
| 5,880,743 | A | * | 3/1999 | Moran et al. | 345/473 |
| 6,020,895 | A | * | 2/2000 | Azami et al. | 345/433 |
| 6,057,844 | A | * | 5/2000 | Strauss et al. | 345/358 |

OTHER PUBLICATIONS

Ethan Winer and Giedt, Brian, "Advanced Graphics in Basic," PC Magazine, Jun. 14, 1988.*

* cited by examiner

Primary Examiner—Raymond J. Bayerl
Assistant Examiner—Thomas J Joseph
(74) Attorney, Agent, or Firm—The Hecker Law Group (57) ABSTRACT

The invention provides a method and apparatus for customizing and substituting strokes provided by a standard API. In a preferred embodiment, a stroke interface that encapsulates stroking algorithms and interfaces for stroke calculation is provided by an API. The stroke interface is provided in the form of a class. The use of the stroke interface permits additional algorithms and interfaces to be provided as new classes. This allows developers to customize stroke characteristics and attributes. In a preferred embodiment, a basic stroke class contains standard stroke characteristics of a logical pen. These characteristics include line width, end cap shape, line join style, and dash attributes.

20 Claims, 4 Drawing Sheets

JOINS

BEVEL  MITER  ROUND

METHOD AND APPARATUS FOR STROKE SUBSTITUTION

BACKGROUND OF THE INVENTION

1. Field of the Invention

This invention relates to the field of computer program development and execution, and more particularly to a method and apparatus for customizing characteristics of strokes used in the generation of computer graphics images.

2. Background Art

In a computer system, it is often desired to create images for outputting via a computer display, a printer, or other output device. Two types of image formats used in computer graphics are "bit-mapped" images and "vector" images. A bit-mapped image (or "raster" image) is stored as a matrix of individual pixels having a defined color and brightness. A vector image is stored as a series of lines or curves (e.g. Bezier curves) having specified endpoints and characteristics such as color, line-style, width, etc. To output a bit-mapped image via a display device, each pixel of the image is mapped to a corresponding pixel of the display. To output a vector image, each line segment of the vector image must first be converted to a corresponding group of pixels that can be mapped to the display.

The lines or curve segments of a vector image may represent outlines of objects, that, when displayed (or "drawn") on an output device, are to be filled with a certain pattern or color. Alternatively, the lines or curves may represent a trajectory or path that, when displayed, is traversed by a series of "strokes" that can be compared to the strokes of a pen or brush. Filling an outline is a fairly straightforward process. Stroking a path or trajectory is more complex, involving determination of the stroke characteristics, such as the shape of the stroke and the style of the pen, for each line or curve segment. Examples of stroke shapes include basic stroke shapes and calligraphic stroke shapes. Examples of pen styles include thick or thin, solid or dashed, etc.

The capability for converting vector images to raster images for display on an output device (i.e. by filling outlines or stroking along stroke trajectories) may be provided by an operating system, or, more typically, by an "application program interface" (API) that provides additional functionality over the operating system. Usually the stroke styles available are limited to some fixed predetermined number provided by the operating environment (operating system and/or API's) of the computer system.

In many environments, when a stroke trajectory is to be drawn by an operating system or API, it is first converted to an outline path called a "stroke outline." This outline is then filled using the same fill capability used to fill other outlined objects. The stroke outline is created by "stroking" along the segments of the stroke trajectory with a logical pen having the characteristics defined for that segment.

The series of pen strokes used to define the stroke trajectory are drawn by the computer. A program developer generally takes advantage of a stroke interface that is part of an API to provide the characteristics of the stroke that is to be used to create an image by the application program being developed. Such an interface permits the developer to select from among the available characteristics of the logical pen provided by the API.

In the prior art most APIs provide a single hard coded algorithm for determining and implementing stroke attributes and characteristics. An interface is provided that allows the application program created by the developer to select from a menu of provided attributes. A hard coded algorithm is then implemented to turn the stroke trajectory into a fillable stroke outline using the selected characteristics. A stroke trajectory is presented to the algorithm and a fillable outline is returned. The fillable outline is then filled using a standard filling algorithm to render the desired strokes.

A disadvantage of the prior art methods of providing a hard coded implementation (API interface and algorithm) is the lack of flexibility to developers and users. Consider a developer who wishes to create a program that uses stroke attributes or characteristics other than those provided in the basic algorithm. For example, it may be desired to have calligraphic style strokes, automatic placement of arrows on the end of lines, or other custom features. To accomplish this in the prior art, the new features must be implemented (if possible) as a manipulation of the stroke outline returned by the basic algorithm. This involves extra rendering steps, additional coding, can degrade performance and in some cases, prevent some desired features.

Alternatively, a developer could implement a custom stroking style by manually turning stroke trajectories into fillable stroke outlines and then using the outline filling API instead of the path stroking API. This has the disadvantage that there is no way to install this custom algorithm into the rendering pipeline so that other arbitrary rendering code which that developer uses, but did not write, will be able to use the custom algorithm.

SUMMARY OF THE INVENTION

The invention provides a method and apparatus for customizing and substituting strokes provided by a standard API. In a preferred embodiment, a stroke interface that encapsulates stroking algorithms and interfaces for stroke calculation is provided by an API. The stroke interface is provided in the form of a class. The use of the stroke interface permits additional algorithms and interfaces to be provided as new classes. This allows developers to customize stroke characteristics and attributes. In a preferred embodiment, a basic stroke class contains standard stroke characteristics of a logical pen. These characteristics include line width, end cap shape, line join style, and dash attributes.

DETAILED DESCRIPTION OF THE INVENTION

A method and apparatus for providing a customizable stroke outline generation interface is described. In the following description, numerous specific details are set forth in detail to provide a more thorough description of the invention. It will be apparent, however, to one skilled in the art, that the invention may be practiced without these specific details. In other instances, well known features have not been described in detail so as not to obscure the invention.

Exemplary Computer System

Figure 1:
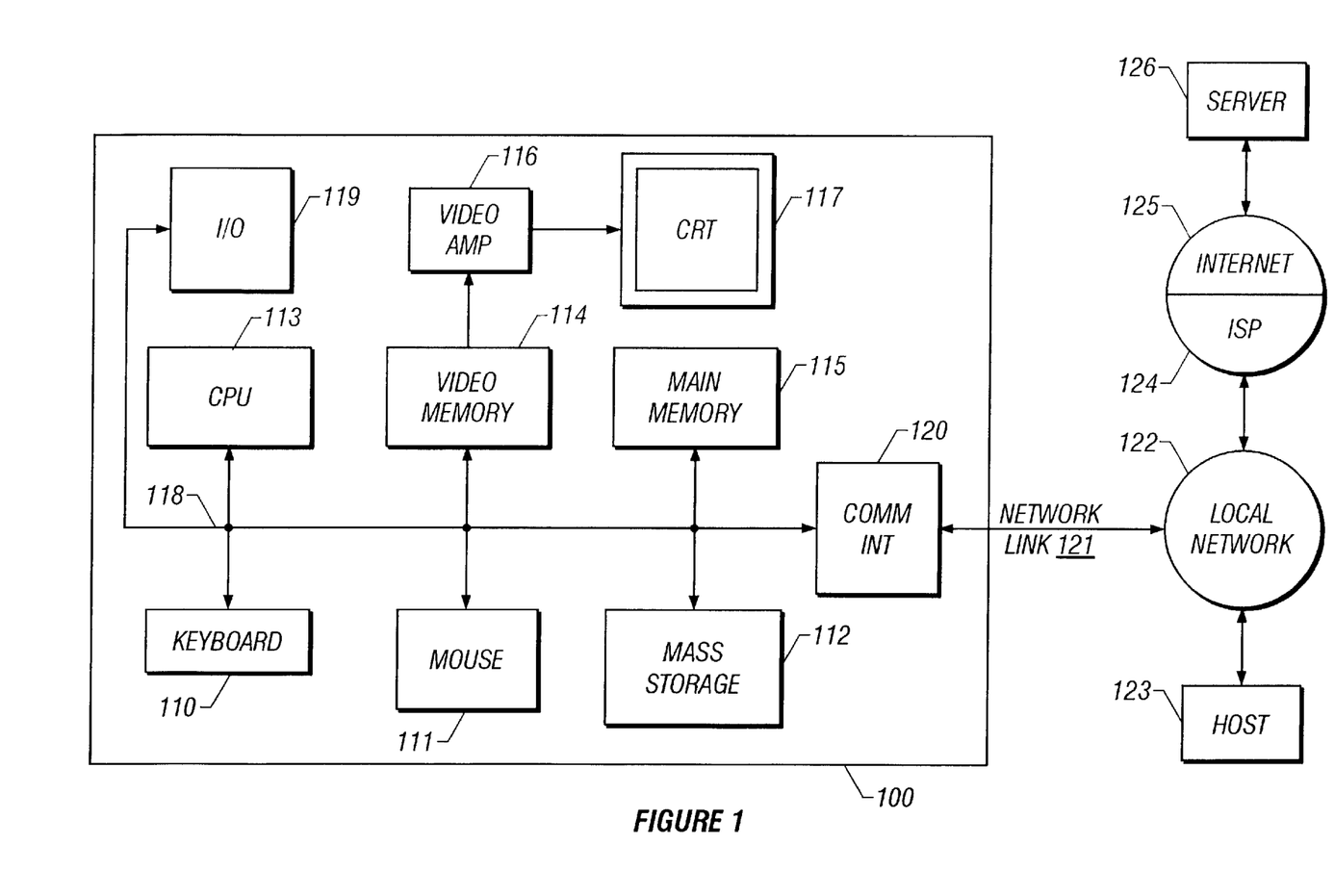
FIG. 1 is a block diagram of a computer system that may be used with an embodiment of the invention.

One or more embodiments of the invention can be implemented as computer software in the form of computer readable program code executed on a general purpose computer such as computer 100 illustrated in FIG. 1. A keyboard 110 and mouse 111 are coupled to a bi-directional system bus 118. The keyboard and mouse are for introducing user input to the computer system and communicating that user input to central processing unit (CPU) 113. Other suitable input devices may be used in addition to, or in place of, the mouse 111 and keyboard 110. I/O (input/output) unit 119 coupled to bi-directional system bus 118 represents such I/O elements as a printer, A/V (audio/video) I/O, etc.

Computer 100 includes a video memory 114, main memory 115 and mass storage 112, all coupled to bi-directional system bus 118 along with keyboard 110, mouse 111 and CPU 113. The mass storage 112 may include both fixed and removable media, such as magnetic, optical or magnetic optical storage systems or any other available mass storage technology. Bus 118 may contain, for example, thirty-two address lines for addressing video memory 114 or main memory 115. The system bus 118 also includes, for example, a 32-bit data bus for transferring data between and among the components, such as CPU 113, main memory 115, video memory 114 and mass storage 112. Alternatively, multiplex data/address lines may be used instead of separate data and address lines.

In one embodiment of the invention, the CPU 113 is a microprocessor manufactured by Motorola, such as the 680X0 processor or a microprocessor manufactured by Intel, such as the 80X86, or Pentium processor, or a SPARC microprocessor from Sun Microsystems. However, any other suitable microprocessor or microcomputer may be utilized. Main memory 115 is comprised of dynamic random access memory (DRAM). Video memory 114 is a dual-ported video random access memory. One port of the video memory 114 is coupled to video amplifier 116. The video amplifier 116 is used to drive the cathode ray tube (CRT) raster monitor 117. Video amplifier 116 is well known in the art and may be implemented by any suitable apparatus. This circuitry converts pixel data stored in video memory 114 to a raster signal suitable for use by monitor 117. Monitor 117 is a type of monitor suitable for displaying graphic images.

Computer 100 may also include a communication interface 120 coupled to bus 118. Communication interface 120 provides a two-way data communication coupling via a network link 121 to a local network 122. For example, if communication interface 120 is an integrated services digital network (ISDN) card or a modem, communication interface 120 provides a data communication connection to the corresponding type of telephone line, which comprises part of network link 121. If communication interface 120 is a local area network (LAN) card, communication interface 120 provides a data communication connection via network link 121 to a compatible LAN. Wireless links are also possible. In any such implementation, communication interface 120 sends and receives electrical, electromagnetic or optical signals which carry digital data streams representing various types of information.

Network link 121 typically provides data communication through one or more networks to other data devices. For example, network link 121 may provide a connection through local network 122 to host computer 123 or to data equipment operated by an Internet Service Provider (ISP) 124. ISP 124 in turn provides data communication services through the world wide packet data communication network now commonly referred to as the "Internet" 125. Local network 122 and Internet 125 both use electrical, electromagnetic or optical signals which carry digital data streams. The signals through the various networks and the signals on network link 121 and through communication interface 120, which carry the digital data to and from computer 100, are exemplary forms of carrier waves transporting the information.

Computer 100 can send messages and receive data, including program code, through the network(s), network link 121, and communication interface 120. In the Internet example, server 126 might transmit a requested code for an application program through Internet 125, ISP 124, local network 122 and communication interface 120. In accord with the invention, one such downloaded application program includes computer readable code for implementing the invention described herein.

The received code may be executed by CPU 113 as it is received, and/or stored in mass storage 112, or other non-volatile storage for later execution. In this manner, computer 100 may obtain application code in the form of a carrier wave.

The computer systems described above are for purposes of example only. An embodiment of the invention may be implemented in any type of computer system or programming or processing environment.

In one or more embodiments, the invention provides a stroke interface that provides standard stroke functionality and customized stroke functionality. In a preferred embodiment of the invention, the stroke interface is implemented as part of the Java 2D API developed by Sun Microsystems, Inc. of Mountain View, Calif.

Java and the Java 2D API

The Java 2D API is an API that provides additional functionality to Java developers and to Java programs.

Java is an object-oriented programming language that can be used to write platform independent computer programs. Unlike programs written with traditional programming languages, Java programs are not distributed in executable form. Instead, Java programs are distributed as packages of "bytecodes." The bytecodes are compiled at runtime into executable code by a Java Virtual Machine (JVM) resident on the computer on which the Java program is run. Different JVM's are used for different computer processors and operating systems. However, all JVM's read the same bytecodes. Accordingly, Java bytecode programs and packages are platform independent. Java bytecode programs and packages need only be written in one form. The JVM's take care of adapting the bytecode to different computer platforms.

Object Oriented Programming

Object-oriented programming is a method of creating computer programs by combining certain fundamental building blocks, and creating relationships among and between the building blocks. The building blocks in object-oriented programming systems are called "objects." An object is a programming unit that groups together a data structure (instance variables) and the operations (methods) that can use or affect that data. Thus, an object consists of data and one or more operations or procedures that can be performed on that data. The joining of data and operations into a unitary building block is called "encapsulation".

An object can be instructed to perform one of its methods when it receives a "message." A message is a command or instruction to the object to execute a certain method. It consists of a method selection (name) and any arguments necessary to perform the method. A message tells the receiving object what operations to perform.

One advantage of object-oriented programming is the way in which methods are invoked. When a message is sent to an object, it is not necessary for the message to instruct the object how to perform a certain method. It is only necessary to request that the object execute the method. This greatly simplifies program development.

Object-oriented programming languages are predominantly based on a "class" scheme. The class-based object-oriented programming scheme is generally described in Lieberman, "Using Prototypical Objects to Implement Shared Behavior in Object-Oriented Systems," OOPSLA 86 Proceedings, September 1986, pp. 214–223.

A class defines a type of object having certain instance variables (properties) and methods (behavior). A class is used to create particular instances of objects. An instance of an object includes the variables and methods defined for the class. Multiple instances of objects of the same class can be created from a class. Each instance that is created from the class is said to be of the same type or class.

A hierarchy of classes can be defined such that a class definition has one or more subclasses. A subclass inherits its parent's (and grandparent's etc.) definition. Each subclass in the hierarchy may add to or modify the behavior specified by its parent class.

To illustrate, an "employee" class can include "name" and "salary" instance variables and a "set_salary" method. Instances of employee objects can be created, or "instantiated," for each employee in an organization. Each object instance is said to be of type "employee." Each employee object instance includes the "name" and "salary" instance variables and the "set_salary" method. The values associated with the "name" and "salary" variables in each employee object instance contain the name and salary of a particular employee. A message can be sent to an employee's employee object instance to invoke the "set_salary" method to modify the employee's salary (i.e., the value associated with the "salary" variable in the employee's employee object).

An object is a generic term that is used in the object-oriented programming environment to refer to a module that contains related code and variables. A software program can be written using an object-oriented programming language whereby the program's functionality is implemented using objects.

Java 2D Graphics2D Objects

Figure 5:
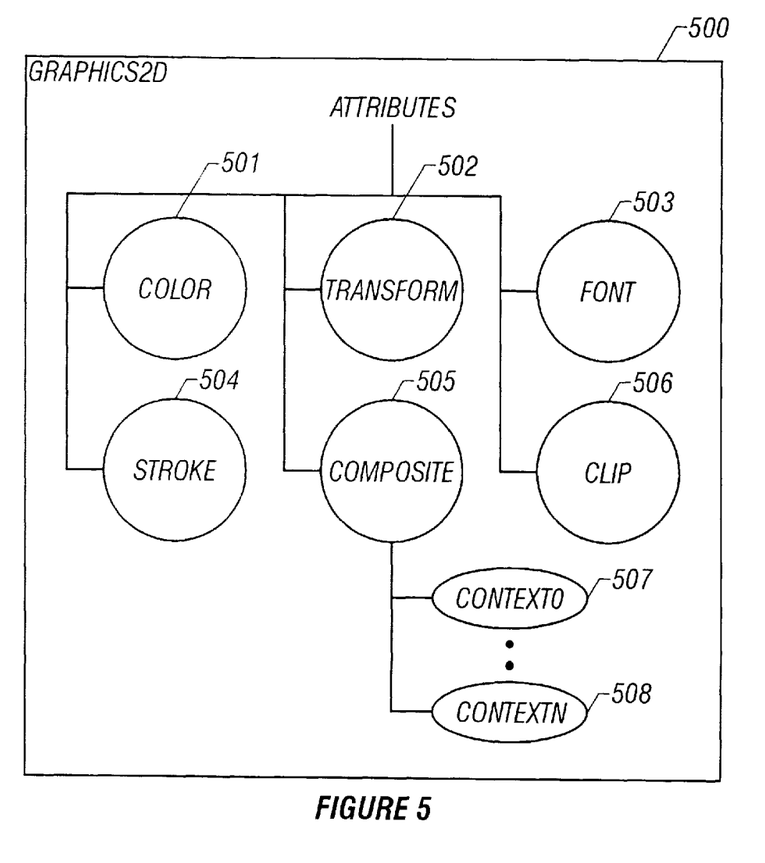
FIG. 5 illustrates an example of a Graphics2D object containing multiple rendering attributes.

The Java 2D API provides a class of drawing objects called "Graphics2D." Graphics 2D objects contain multiple rendering attributes that specify how particular rendering operations should be performed. FIG. 5 illustrates a sample Graphics2D object that contains multiple rendering attributes. In FIG. 5, Graphics2D object 500 contains the following attributes: Color 501, Transform 502, Font 503, Stroke 504, Composite 505, and Clip 506. These attributes are represented by objects that contain rendering behavior definitions, including behavior parameters and methods for setting the parameters.

For example, Color 501 contains information regarding the color value of a drawing operation, and has constructors for creating Color objects with specific color values. Transform 502 contains information on a geometric transformation. Font 503 may contain information such as font style and family definitions for text drawing operations. Stoke 504 may contain pen style information such as pen shape and width, and line segment characteristics.

The Stroke attributes of a Graphics2D object may be set by means of the "setStroke" method, and may be retrieved from a Graphics2D object by means of the "getStroke" method.

Embodiments of the Invention

In one or more embodiments of the invention, shape, path, and stroke objects are provided. Shape objects are objects that represent various kinds of shapes contained in an image, including, for example, rectangles, circles, and other regular and irregular shapes. In one or more embodiments, a shape object includes a path object that expresses the outline of the shape using a sequence of straight lines and 2nd and 3rd order Bezier curves. In a preferred embodiment, such an object is referred to as a "path iteration object." Drawing, or "rendering," of a shape object is accomplished by retrieving the path iteration object from the shape object, and then stroking and filling the outline. Stroking a shape object is equivalent to running a logical pen along the sequence of segments of the shape's outline. In one or more embodiments, a stroke object encapsulates the characteristics of the line or mark (stroke) drawn by the pen. In one or more embodiments, characteristics of the stroke object are determined by means of a stroke "interface."

Stroke Interface

In one or more embodiments of the invention, stroke rendering operations include methods that are defined using the "interface" mechanisms of the Java programming language. In the Java language, an interface consists of a collection of constants and abstract methods. A class can implement an interface by adding the interface to the class's "implements" clause. When an interface is implemented by a class, the abstract methods of the interface can be overridden (i.e. replaced). A variable can be declared as an interface type and all of the constants and methods declared in the interface can be accessed from this variable.

A preferred embodiment of the invention includes an interface called "Stroke." This interface allows a drawing object (such as, for example, a "Graphics2D" object of the Java 2D API) to obtain a representation of a stroke outline that defines the boundaries of a stroking primitive along a stroke trajectory. The effect of stroking along a stroke trajectory can be compared to drawing a logical pen of an appropriate size and shape along the stroke trajectory. The area where the pen would place ink is the area enclosed by the stroke outline.

In a preferred embodiment, the stroking primitives of the stroke interface include a "drawPath" method and other methods that are implemented in terms of the drawPath method. These other methods may include, for example, "drawLine", "drawRect", "drawRoundRect", "drawOval", "drawArc", "drawPolyline", and "drawPolygon" methods.

In a preferred embodiment, the stroke interface includes a method called "createStrokedShape." The createStrokedShape method returns a shape object which defines the stroke outline or area that should be painted when the stroke trajectory for the shape object is stroked according to the rules defined by the class, or object, implementing the stroke interface. In this embodiment, the createStrokedShape method receives the stroke trajectory that should be stroked as an input parameter, and returns the stroke outline.

BasicStroke Class

In a preferred embodiment of the invention, the stroke interface is implemented by a class called "BasicStroke." This class defines a set of rendering attributes for stroked graphics primitives. These attributes describe the shape of a pen that is to be drawn along the stroke trajectory and the decorations to be applied where segments are joined and where they begin and end. In a preferred embodiment, these attributes include:

"width"—The width of the pen measured perpendicular to its trajectory.

"end caps"—The shape of the stroke outline where line segments begin and end.

"line joins"—The shape of the stroke outline between connected line segments.

"dash attributes"—The definition of how to make a dash pattern along the stroke trajectory by creating new segments which alternate between opaque and transparent sections.

Figure 2A:
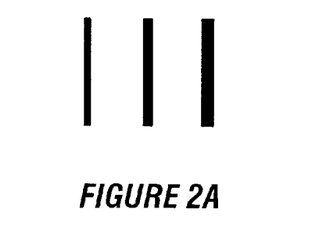
FIGS. 2A–2D illustrate examples of stroke characteristics.
Figure 2B:
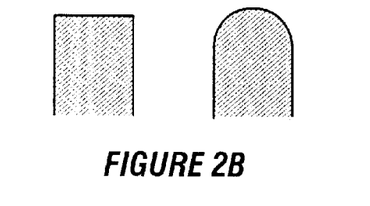
Figure 2C:
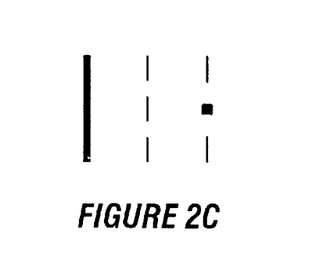
Figure 2D:
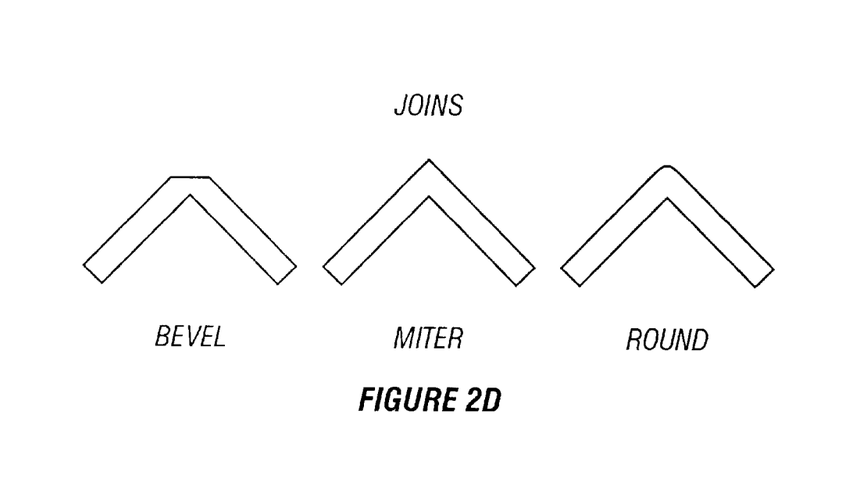

Examples of stroke styles that can be implemented using the BasicStroke class in a preferred embodiment are illustrated in FIGS. 2A–2D. FIG. 2A illustrates a selection of example line widths ranging from thinner lines on the left to thicker lines to the right. FIG. 2B illustrates examples of different kinds of end-caps. An end-cap defines how the end of the line appears when it is not connected to any other lines. The end-caps of FIG. 2B include a squared off end cap on the left and a round end cap on the right. FIG. 2C illustrates examples of different dashing patterns. The line on the left has no dashing pattern (i.e. is a continuous line), the line in the middle has equally sized dashed sections, while the line on the right has a dash-dot pattern. FIG. 2D illustrates examples of different join styles. The join styles illustrated in FIG. 2D, going from left to right, are bevel, miter and round join styles.

The attributes described above are given by way of example, only. Other attributes or other variations of these attributes may be used without departing from the scope of the invention.

Figure 3:
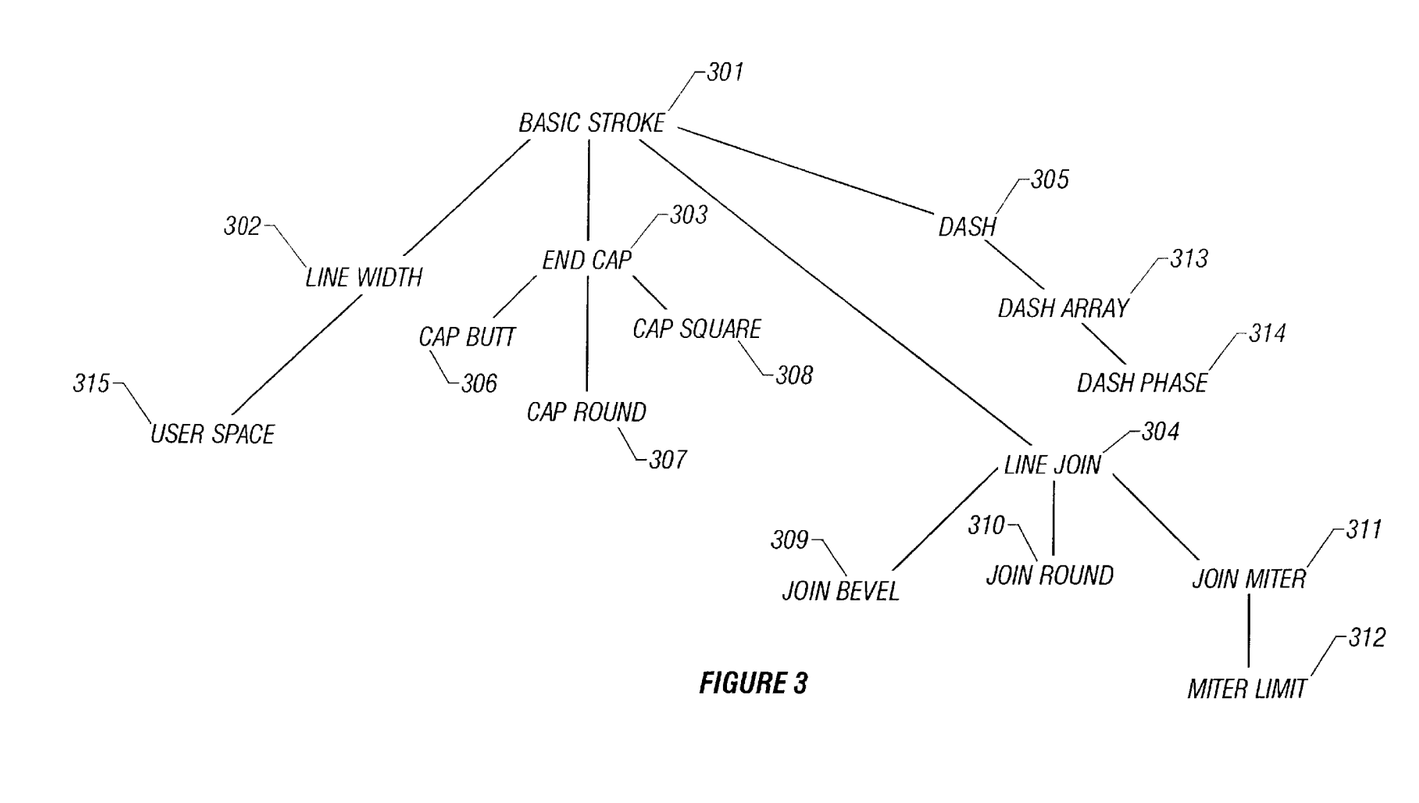
FIG. 3 illustrates an example of an object class of the invention.

FIG. 3 illustrates an example of a class used in one or more embodiments of the invention. BasicStroke class 301 represents an accessible source of common stroking information. BasicStroke class 301 contains information regarding a stroke to be rendered. For example, BasicStroke class 301 has associated methods for defining linewidth 302, endcap 303, linejoin 304, and dash 305. Linewidth 302 represents the width of the line to be stroked as represented (displayed to a user) in user space 315.

Endcap 303 represents the type of finish on a rendered line segment. The endcap may be capButt 306, capRound 307, or capSquare 308. Linejoin 304 represents the style of the intersection of two line segments. The style of the intersection (join) may be joinBevel 309, joinRound 310, or join-Miter 311. JoinMiter 311 is further defined by MiterLimit 312.

Dash 305 represents the presence or absence, as well as pattern, of dashing of the stroked line segments. DashArray 313 represents lengths of dash segments and of spaces between dash segments. DashPhase 314 represents an initialized distance accumulation variable defining the length of a space before the first segment is stroked.

Variables

In a preferred embodiment, the variables of the Basic-Stroke class include variables to define endcaps and joins. In a preferred embodiment, these variables include:

CAP_BUTT (public final static int CAP_BUTT)
  The CAP_BUTT variable specifies that the ends of unclosed subpaths in the stroke trajectory and of dash segments are to be provided with no added decoration in the stroke outline.
CAP_ROUND (public final static int CAP_ROUND)
  The CAP_ROUND variable specifies that the ends of the stroke outline for unclosed subpaths in the stroke trajectory and of dash segments are to be capped off with a round decoration having a radius equal to half of the line width.
CAP_SQUARE (public final static int CAP_SQUARE)
  The CAP_SQUARE variable specifies that the stroke outlines of unclosed subpaths in the stroke trajectory and of dash segments are to be capped off by adding a square projection to the stroke outline that extends beyond the end of a stroke segment to a distance equal to half of the line width.
JOIN_BEVEL (public final static int JOIN_BEVEL)
  The JOIN_BEVEL variable specifies that line segments are to be joined by connecting the outer corners of their wide stroke outlines with a straight segment.
JOIN_MITER (public final static int JOIN_MITER)
  The JOIN_MITER variable specifies that line segments are to be joined by extending the outside edges of their wide stroke outlines until they meet.
JOIN_ROUND (public final static int JOIN-ROUND)
  The JOIN_ROUND variable specifies that line segments are to be joined by rounding off the corners of their wide stroke outlines at a radius of half the line width.

Constructors

Constructors used to create instances of the BasicStroke class in a preferred embodiment include:

BasicStroke()
  public BasicStroke ()
  This constructor constructs a new stroke with defaults for all attributes.
  The default attributes are a line width of 1.0, CAP_BUTT, JOIN_MITER, a miter limit of 1.0, and no dashing.

BasicStroke (float, int, int)
  public BasicStroke (float width, int cap, int join)
  This constructor constructs a new stroke with attributes as specified by the width, cap, and join parameters, with no dashing.
  The parameters used by this constructor are defined as follows:
    width—The width of the stroke.
    cap—The style of the ends of a stroke.
    join—The style to join strokes together.

Basic Stroke (float, int, int, float)
  public BasicStroke (float width, int cap, int join, float miterlimit)
  This constructor constructs a new stroke with the attributes specified by the width, cap, join, and miterlimit parameters, with no dashing.
  The parameters used by this constructor are defined as follows:
    width—The width of the stroke.
    cap—The style of the ends of a stroke.
    join—The style to join strokes together.
    miterlimit—The limit to trim the miter join.

Basic Stroke (float, int, int, float, float [ ], float)
  public BasicStroke (float width, int cap, int join, float miterlimit, float dash [ ], float dash_phase)
  This constructor constructs a new stroke with the attributes specified by the width, cap, join, miterlimit, dash, and dash_phase parameters.
  The parameters used by this constructor are defined as follows:
    width—The width of the stroke.
    cap—The style of the ends of a stroke.
    join—The style to join strokes together.
    miterlimit—The limit to trim the miter join.
    dash—the array representing the dashing pattern.
    dash_phase—The offset to start the dashing pattern.

Methods

Methods that can be used with the BasicStroke class in a preferred embodiment include "createStrokedShape," "getLineWidth," "getEndCap," "getLineJoin,"

"getMiterLimit," "getDashArray," and "getDashPhase." These methods are described in more detail below.

createStrokedShape public Shape createStrokedShape (Shape p)

This method returns the stroke outline of a given stroke trajectory specified by the parameter p.

getLineWidth public float getLineWidth()

This method returns the line width represented in the user space.

getEndCap public int getEndCap()

This method returns the end cap style.

getLineJoin public int getLineJoin()

This method returns the line join style.

getMiterLimit public float getMiterLimit()

This method returns the limit of miter joins.

getDashArray public float [ ]getDashArray()

This method returns the array representing the lengths of the dash segments. Alternate entries in the array represent the user space lengths of the opaque and transparent segments of the dashes. As the pen moves along the stroke trajectory, the user space distance that the pen travels is accumulated to index into the dash array. The pen is opaque when its current cumulative distance maps to an odd element of the dash array and transparent otherwise.

getDashPhase public float getDashPhase()

This method returns the dash phase. The dash phase is a user space distance that is used to initialize the stroke trajectory distance accumulation variable before the first segment of the first subpath of the stroke trajectory is stroked.

Customizing Stroke Implementations

Figure 4:
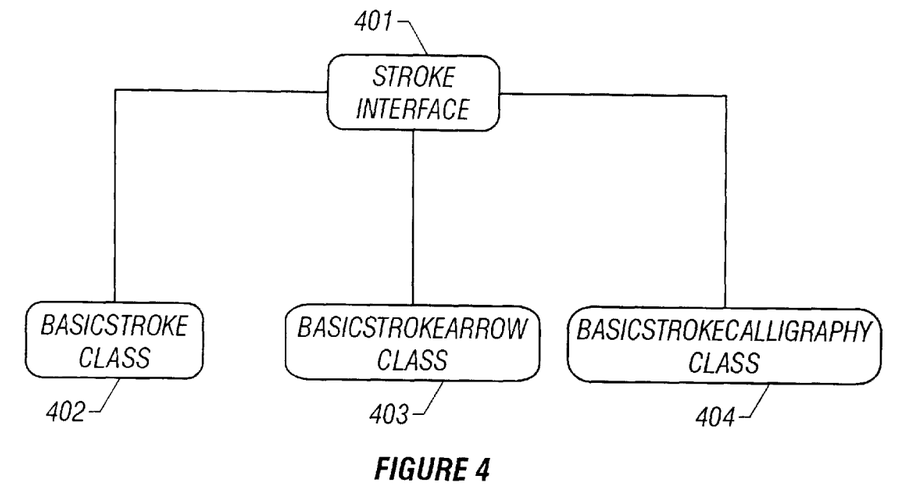
FIG. 4 illustrates and example of object classes that implement a stroke interface in an embodiment of the invention.

Additional stroke styles may be added by defining additional classes that implement the stroke interface. In FIG. 4, a number of classes that implement the stroke interface 401 are illustrated. BasicStroke class 402 is the class described in connection with FIGS. 2 and 3. BasicStrokeArrow class 403 is an example of a class that produces stroke outlines that have arrowheads on the ends of line segments. BasicStrokeCalligraphy class 404 is an example of a class that produces stroke outlines that have a calligraphic style. In a preferred embodiment, classes that implement the stroke interface (both standard and custom classes) include the method "createStrokedShape." Customized classes preferably also include constructors, which may or may not take the same format as the constructors described above in connection with the BasicStroke class.

By implementing a stroke interface as a class, customized stroke characteristics and attributes can be easily added as new classes without rewriting basic coded algorithms.

Thus, a method and apparatus for customizing stroke attributes and stroke substitution has been described.

What is claimed is:

1. In a computer program for manipulating graphical objects, a method for customizing and substituting stroke outlines and interfaces, using an object oriented architecture, said method comprising:

providing one or more shape, path and stroke object classes;

providing a plurality of stroke rendering operations defined in at least one stroke interface object class using an "interface" mechanism, wherein said providing said plurality of stroke rendering operations provides a developer with the ability to dynamically insert custom stroke object classes;

providing, in said at least one stroke interface object class, a plurality of attribute variables configured to define control states of said plurality of stroke rendering operations;

obtaining a stroked graphical object class representing a graphical object using an "implements" mechanism to implement said at least one stroke interface object class;

obtaining a representation of a stroke outline of said stroked graphical object defining the boundaries of a stroking primitive along a stroke trajectory;

providing a source of common stroking information associated with said at least one stroked graphical object;

obtaining stroking information of said stroked graphical object using said source of common stroking information;

rendering said graphical object stroke outlines using at least one of said plurality of stroke rendering operations and at least one of said plurality of attribute variables.

2. The method of claim 1 wherein said stroke interface object class comprises a method for obtaining a stroked shape.

3. The method of claim 1 wherein said stroke interface object class is implemented by a basic stroke class.

4. The method of claim 3 wherein said basic stroke class defines stroke class defines stroke attributes including line width, end cap, join style, and dash pattern.

5. The method of claim 3 wherein said basic stroke class comprises:

a first variable that specifies that ends of unclosed subpaths in a stroke trajectory and of dash segments are to be provided with no added decoration;

a second variable that specifies that the ends of unclosed subpaths in a stroke trajectory and of dash segments are to be capped off with a round decoration having a radius equal to half of a line width;

a third variable that specifies that the stroke outlines of unclosed subpaths in the stroke trajectory and of dash segments are to be capped off by adding a square projection to the stroke outline that extends beyond an end of a stroke segment to a distance equal to half of a line width;

a fourth variable that specifies that line segments are to be joined by connecting outer corners of their stroke outlines with a straight segment;

a fifth variable that specifies that line segments are to be joined by extending outside edges of their stroke outlines until they meet;

a sixth variable that specifies that line segments are to be joined by rounding off corners of their stroke outlines at a radius of half as line width.

6. The method of claim 5 wherein said stroke interface comprises a method for obtaining a stroked shape.

7. The method of claim 5 wherein said basic stroke class comprises:

a first method for obtaining a stroked shape;

a second method for returning a line width;

a third method for returning an end cap style;

a fourth method for returning a line join style;

a fifth method for returning a milter limit;

a sixth method for returning a dash configuration;

a seventh method for returning a dash phase.

8. A computer program embodied in a tangible medium comprising computer readable program code tangibly embodying a program of instructions to cause a computer processor to perform method steps for customizing and substituting stroke outlines and interfaces, said method comprising:

provuding one or more shape, path and stroke object classes;

providing a plurality of stroke rendering operations defined in at least one stroke interface object class using an "interface" mechanism, wherein said providing said plurality of stroke rendering operations provides a developer with the ability to dynamically insert custom stroke object classes;

providing, in said at least one stroke interface object class, a plurality of attribute variables configured to define control states of said plurality of stroke rendering operations;

obtaining a stroked graphical object class representing a graphical object using an "implements" mechanism to implement said at least one stroke interface object class;

obtaining a representation of a stroke outline of said stroked graphical object defining the boundaries of a stroking primitive along a stroke trajectory;

providing a source of common stroking information associated with said at least one stroked graphical object;

obtaining stroking information of said stroked graphical object using said source of common stroking information;

rendering said graphical object stroke outlines using at least one of said plurality of stroke rendering operations and at least one of said plurality of attribute variables.

9. The computer program embodied in a tangible medium of claim 8 wherein said stroke interface comprises a method for creating a stroked shape.

10. The computer program embodied in a tangible medium of claim 9 wherein said basic stroke class defines stroke attributes including line width, end cap, join style, and dash pattern.

11. The computer program embodied in a tangible medium of claim 9 wherein said basic stroke class comprises;

a first variable that specifies that ends of unclosed subpaths in a stroke trajectory and of dash segments are to be provided with no added decoration;

a second variable that specifies that the ends of unclosed subpaths in a stroke trajectory and of dash segments are to be capped off with a round decoration having a radius equal to half of a line width;

a third variable that specifies that the stroke outlines of unclosed subpaths in the stroke trajectory and of dash segments are to be capped off by adding a square projection to the stroke outline that extends beyond an end of a stroke segment to a distance equal to half of a line width;

a fourth variable that specifies that line segments are to be joined by connection outer corners of their stroke outlines with a straight segment;

a fifth variable that specifies that line segments are to be joined by extending outside edges of their strike outlines until they meet;

a sixth variable that specifies that line segments are to be joined by rounding off corners of their stroke outlines at a radius of half as line width.

12. The computer program embodied in a tangible medium of claim 8 wherein said stroke interface comprises a method for creating a stroked shape.

13. The computer program embodied in a tangible medium of claim 11 wherein said basic stroke class comprises:

a first method for creating a stroked shape;

a second method for returning a line width;

a third method for returning an end cap style;

a fourth method for returning a line join style;

a fifth method for returning a miter limit;

a sixth method for returning a dash configuration;

a seventh method for returning dash phase.

14. A system comprising:

a processor;

a memory;

code executed by said processor configured to define, obtain, substitute and customize stroke outlines and interfaces, said code comprising:

providing one or more shape, path and stroke object classes;

providing a plurality of stroke rendering operations defined in at least one stroke interface object class using an "interface" mechanism, wherein said providing said plurality of stroke rendering operations provides a developer with the ability to dynamically insert custom stroke object classes;

providing, in said at least one stroke interface object class, a plurality of attribute variables configured to define control states of said plurality of stroke rendering operations;

obtaining a stroked graphical object class representing a graphical object using an "implements" mechanism to implement said at least one stroke interface object class;

obtaining a representation of a stroke outline of said stroked graphical object defining the boundaries of a stroking primitive along a stroke trajectory;

providing a source of common stroking information associated with said at least one stroked graphical object;

obtaining stroking information of said stroked graphical object using said source of common stroking information;

rendering said graphical object stroke outlines using at least one of said plurality of stroke rendering operations and at least one of said plurality of attribute variables.

15. The system of claim 14 wherein said stroke interface comprises a method for obtaining a stroked shape.

16. The system of claim 14 wherein said stroke interface is implemented by a basic stroke class.

17. The system of claim 16 wherein said basic stroke class defines stroke attributes including line width, end cap, join style, and dash pattern.

18. The system of claim 16 wherein said basic stroke class comprises:

a first variable that specifies that ends of unclosed subpaths in a stroke trajectory and of dash segments are to be provided with no added decoration;

a second variable that specifies that the ends of unclosed subpaths in a stroke trajectory and of dash segments are to be capped off with a round decoration having a radius equal to half of a line width;

a third variable that specifies that the stroke outlines of unclosed subpaths in the stroke trajectory and of dash segments are to be capped off by adding a square projection to the stroke outline that extends beyond an end of a stroke segment to a distance equal to half of a line width;

a fourth variable that specifies that line segments are to be joined by connecting out corners of their stroke outlines with a straight segment;

a fifth variable that specifies that line segments are to be joined by extending outside edges of their stroke outlines until they meet;

a sixth variable that specifies that line segments are to be joined by rounding off corners of their stroke outlines at a radius of half as line width.

19. The system of claim 18 wherein said stroke interface comprises a method configured to obtain a stroked shape.

20. The system of claim 18 wherein said basic stroke class comprises:

a first method configured to obtain a stroked shape;

a second method configured to return an end cap style;

a fifth configured to return a miter limit;

a sixth method configured to return a dash configuration;

a seventh method configured to return a dash phase.

* * * * *